United States Patent [19]

Teshima et al.

[11] 4,155,351

[45] May 22, 1979

[54] MEDICAL INSTRUMENT FOR DETECTING BODY IMPEDANCE

[75] Inventors: Toru Teshima, Hadano; Akira Iwamatsu, Tokyo; Yoshinori Uchiyama, Machida; Hoichiro Kashiwabara, Tokyo, all of Japan

[73] Assignee: Stanley Electric Co., Ltd., Tokyo, Japan

[21] Appl. No.: 798,184

[22] Filed: May 18, 1977

[30] Foreign Application Priority Data

May 21, 1976 [JP] Japan .................................. 51/65177
May 22, 1976 [JP] Japan .................................. 51/59465

[51] Int. Cl.² .......................... A61B 5/05; A61H 39/02
[52] U.S. Cl. .................................. 128/734; 128/2.1 C
[58] Field of Search ............... 128/2.1 R, 2.1 C, 2.1 E, 128/2.1 Z, 1.4, 303.1, 303.13, 303.14, 303.17, 303.18, 303.19, 172.1, 405, 406, 409; 324/53

[56] References Cited

U.S. PATENT DOCUMENTS

| 1,696,266 | 12/1928 | Coote ..................................... 324/53 |
| 2,659,372 | 11/1973 | Andresen ............................. 128/406 |
| 2,666,894 | 1/1954 | Babernitsh ............................ 324/53 |
| 3,625,222 | 12/1971 | Shimizu ............................... 128/405 |
| 3,755,900 | 9/1973 | Friedman ....................... 128/2.1 R X |
| 3,830,226 | 8/1974 | Staub et al. ........................ 128/2.1 R |
| 3,943,919 | 3/1976 | Landgraf ........................... 128/2.1 R |

FOREIGN PATENT DOCUMENTS

| 990296 | 4/1965 | United Kingdom ................. 128/2.1 C |
| 1126634 | 9/1968 | United Kingdom ................. 128/2.1 C |
| 1416141 | 12/1975 | United Kingdom ................. 128/2.1 C |

*Primary Examiner*—Lee S. Cohen
*Attorney, Agent, or Firm*—Frishauf, Holtz, Goodman and Woodward

[57] ABSTRACT

A medical cell holder for use in a device which detects the impedance of a human body to actuate an electronic circuit. The holder comprises an inner assembly containing an electronic circuit; and a metallic ornamental casing having a switch mechanism at one end thereof. A cell (i.e. a battery) and the assembly are contained in said casing with the cell and the electronic circuit connected in series through the switch mechanism. The casing constitutes one electrode, which is portable in hand and which provides electrical contact with a human body.

3 Claims, 2 Drawing Figures

MEDICAL INSTRUMENT FOR DETECTING BODY IMPEDANCE

BACKGROUND OF THE INVENTION

The present invention relates to a medical instrument, such as an instrument for diagnosing ears, a device for detecting a particular point of human body, or the like, and more particularly to a medical cell holder which contains an electronic circuit and cell therein and which is used as an electrical ground connection for the human body.

In such a medical instrument, separate parts are generally provided to serve as a body incorporating an electronic circuit, a metallic ground bar for a human body and a searching bar. The ground bar and the searching bar are each connected by means of a cord or a wire to the body which is generally set on a table. When using such a medical instrument, a patient or a person to be inspected having no electrical knowledge shows his mental refusal to gripping of the metallic ground bar which is passing electrical current even if the electrical current is very small. Such mental problems cause adverse effects during diagnosis or treatment. There is also a problem to provide each separate cord or wire as mentioned above. The searching bar does not reach to a desired portion for treating and searching when the cords are short in length and further, the body may be caused to fall from the table and to damage it, by pulling the searching bar to reach the desired portion. Adversely, when the cords are long in length, since the cords of the ground bar and the searching bar are maintained together upon transporting or when the device is not in use, they intertwine with each other and much time is required to untangle them. Further, bad connections may arise between the cord and the connector and between the cord and the ground bar or the searching bar because of excessive touching and excessive force applied to the connecting portions.

To eliminate the above defects, it is an object of the present invention to provide a medical cell holder which has no metallic ground bar, thereby to remove intertwinement between its cord and a cord of a searching bar, and which does not impart mental pain or anxiety to a person to be inspected when using its compact body as a ground electrode.

It is another object of the invention to provide a medical cell holder which provides a cover having a switch mechanism while still maintaining an attractive appearance.

SUMMARY OF THE INVENTION

According to the invention, there is provided a medical cell holder for use in a device adapted to detect the impedance of a human body to actuate an electronic circuit, characterized in that the holder comprises an inner assembly containing an electronic circuit, and a metallic ornamental casing formed independently from said inner assembly and having a switch mechanism at one end of the casing, said ornamental casing receiving therein a cell and paid inner assembly with the cell and the electronic circuit connected in series through said switch mechanism. The cell holder is portable and serves as one electrode contacting with human body.

DETAILED DESCRIPTION

Figure 1:
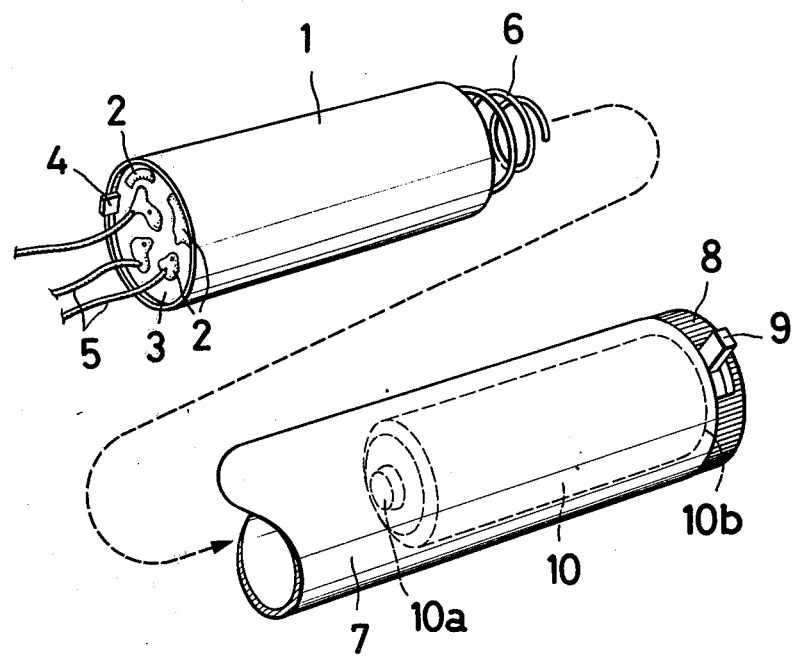
FIG. 1 is a pictorial view showing a medical cell holder according to the invention having essential portions separated.

Referring to FIG. 1, an inner metallic housing assembly 1 contains a printed board 3 having an electronic circuit 2 thereon. The printed board 3 and the inner housing assembly 1 are fixed together by a connecting piece 4 formed on one end of the assembly 1 and are insulated from each other so as not to electrically form a shortcircuit to each other. A plurality of cords or wires 5 are taken out from the electronic circuit 2 to an output terminal (or connector) to which a searching bar or an indicating part (not shown) is connected. A coil spring 6 is disposed at one end of the assembly 1 opposite to the electronic circuit 2 so as to electrically connect to the electronic circuit 2.

An ornamental casing 7 of metal is formed independently of the assembly 1 so as to be capable of receiving the assembly 1 therein. A cover 8 is threadably secured at a rear end of the ornamental casing 7 and includes a switch mechanism which is capable of carrying out its switching action by means of a knob 9 protruding from the cover.

A cell (i.e., a battery) 10 is contained in the ornamental casing 7. A plus terminal 10a of the cell is connected in series to the electronic circuit 2 through the coil spring 6 and a minus terminal 10b is connected in series to the ornamental casing 7 through the switch mechanism cover 8. Accordingly, the assembly 1 is protected by the ornamental casing 7 and a series circuit is formed by the electronic circuit 2, the cell 10, the switch mechanism and the ornamental casing 7.

If, the switch mechanism is turned on in use, since the ornamental metal casing 7 becomes one electrode of the series circuit it is advantageous to permit the patient or the person to be inspected to grasp the ornamental casing to provide an electrical connection to the patient or the person being inspected.

Figure 2:
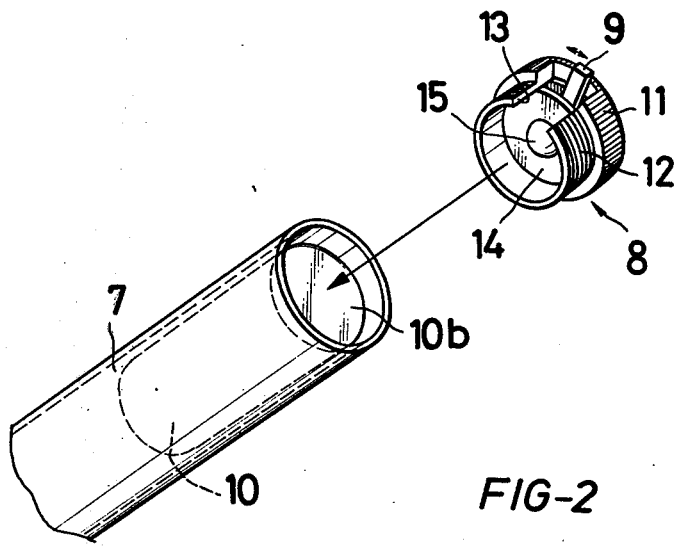
FIG. 2 is a perspective view showing a cover which forms part of the medical cell holder according to the invention.

Referring to FIG. 2, there is shown in detail the cover 8 which secures the cell 10 in the ornamental casing 7 and which closes one end of the latter. The cover 8 is provided with a base portion 11 and a fitting portion 12 formed integrally. The base portion 11 has a knurled or grooved peripheral surface. The fitting portion 12 is threaded and is provided with a cut out portion 13 at one side surface thereof. Into the cover 8 is interposed, for example, a printed board 14 which is mounted on a terminal 15 contacting with an electrode 10b of the cell 10 and a knob 9 for turning on or off the circuit, the knob 9 protruding outwards from the cut out portion 13. Accordingly, if the cover 8 is screwed onto to the ornamental casing 7, the circuit is formed through the electrode 10b of the cell 10, the circuit being turned on or off by means of the knob 9.

As understood from the above description, since the cover 8 is provided with the switch mechanism, it is not necessary to provide means for mounting the switch mechanism on the ornamental casing 7. Accordingly, the cover 8 is very useful in function in respect to the instrument which is portable in hand according to the invention. Further, the cover 8 has an advantage that repairing and checking is easily realized if the switch malfunctions.

The medical cell holder having a structure described above receives the assembly 1 having the electronic circuit 2 and the cell 10 in the ornamental casing 7 and the casing 7 is used as a body of the medical instrument. Further, because the cell holder is compact to use as an electrode to apply electrical current to the human body and is portable in hand, the patient or the person to be inspected can grasp the holder without feeling mental pain or anxiety. Since only one cord is taken out from the holder to connect with the searching bar, intertwinement between cords as in the prior art is obviated. Furthermore, since the electronic circuit is doubly protected by the assembly and the ornamental casing its shock resistance is large.

It is further understood by those skilled in the art that the foregoing description is a preferred embodiment of the device and that various changes and modifications may be made in the invention without departing from the spirit and scope thereof as defined in the appended claims.

What is claimed is:

1. A medical instrument for detecting the impedance of the human body by making selective electrical contact therewith, comprising:

a substantially cylindrical metallic ornamental outer casing;

a substantially cylindrical metallic inner housing removably received in said outer casing, said inner housing and outer casing being in electrical contact with each other;

an electronic impedance detecting circuit contained within said inner housing and electrically insulated from said inner housing;

said outer casing including means at one end thereof for receiving a battery power source;

said inner housing being contained within said outer casing and adopted to be adjacent a received battery power source and including connecting means for connecting said electronic circuit to a terminal of a received battery power source;

an end cap removably secured to said one end of said outer casing to retain a received battery power source and said inner housing within said outer casing, said end cap comprising a switch means for selectively connecting the other terminal of a received battery power source to said metallic outer casing, said switch means having "on" and "off" positions;

whereby a received battery power source and electronic circuit contained within said inner housing are electrically connected in series with said metallic casing through said switch means; and electrically conducting lead wires extending from said electronic circuit to outside said outer casing and being electrically insulated from said outer casing for selectively contacting parts of a human body, said outer casing being adapted to be held by a human being so as to make constant electrical contact with the human body.

2. The medical instrument of claim 1 wherein said end cap is threadably connected to said one end of said outer casing.

3. The medical instrument of claim 1 wherein said connecting means for connecting said electronic circuit to a terminal of a received battery power source comprises a metallic coil spring extending from said inner housing and electrically insulated from said inner housing and adapted to contact said terminal of a received battery power source.

* * * * *